US00PP30009P3

(12) United States Plant Patent
Brisset et al.

(10) Patent No.: US PP30,009 P3
(45) Date of Patent: Dec. 25, 2018

(54) APPLE TREE NAMED 'GALA SURF'

(50) Latin Name: *Malus domestica*
Varietal Denomination: Gala Surf

(71) Applicant: International Fruit Obtention (IFO) GIE, Seiches sur le Loir (FR)

(72) Inventors: Frédéric Brisset, Soeurdres (FR); David Brisset, Soeurdres (FR)

(73) Assignee: International Fruit Obtentións (IFO) GIE, Seiches sur le Loir (FR)

( * ) Notice: Subject to any disclaimer, the term of this patent is extended or adjusted under 35 U.S.C. 154(b) by 0 days.

(21) Appl. No.: 15/330,389

(22) Filed: Sep. 12, 2016

(65) Prior Publication Data

US 2018/0077833 P1 Mar. 15, 2018

(51) Int. Cl.
*A01H 5/08* (2018.01)
*A01H 6/74* (2018.01)

(52) U.S. Cl.
USPC ..... Plt./162
CPC ..... *A01H 6/7418* (2018.05); *A01H 5/08* (2013.01)

(58) Field of Classification Search
USPC ..... Plt./162
CPC ..... A01H 5/0875
See application file for complete search history.

(56) References Cited

PUBLICATIONS

GTITM UPOVROM Citation for 'Gala Surf' as per QZ PBR 20150021; Apr. 15, 2015; 1 page.*

* cited by examiner

*Primary Examiner* — Kent L Bell
(74) *Attorney, Agent, or Firm* — Michelle Bos Legal LLC

(57) ABSTRACT

'Gala Surf' is a sport mutation of 'Gala'. The fruit of 'Gala Surf' is notable for its early coloring and very dark purple red overcolor.

5 Drawing Sheets

Latin name: *Malus domestica.*
Variety denomination: 'Gala Surf'.

BACKGROUND OF THE VARIETY

'Gala Surf' is a new and distinct variety of apple tree (*Malus domestica*). 'Gala Surf' is a natural whole tree mutation of 'Gala' (U.S. Plant Pat. No. 3,637) discovered by the inventors in an established 'Gala' orchard at Soeurdres, France in 2012. Propagative material of the newly discovered tree was asexually reproduced by budding at Doué la Fontaine, France in 2012 and subsequently fruited through successive generations at Doué la Fontaine, France. 'Gala Surf' has been observed to remain true to type over successive asexually propagated generations.

BRIEF DESCRIPTION OF THE VARIETY

'Gala Surf' was first selected for its very dark purple red overcolor as compared to the bright red overcolor of parent 'Gala'. Comparisons of 'Gala Surf' to similar 'Gala'-type varieties are shown in the following tables.

TABLE 1

Comparison of 'Gala Surf' to 'Simmons' (U.S. Plant Pat. No. 10,840)

| | "Gala Surf' | 'Simmons' |
|---|---|---|
| Petiole: extent of anthocyanin coloration from base | Large | Medium |
| Young fruit: extent of anthocyanin overcolor | Medium to large | Medium |

TABLE 1-continued

Comparison of 'Gala Surf' to 'Simmons' (U.S. Plant Pat. No. 10,840)

| | "Gala Surf' | 'Simmons' |
|---|---|---|
| Fruit: Overcolor | Very dark purple red | Purple red |
| Time of coloration | Earlier | Later |
| Time of eating maturity | Later | Earlier |

TABLE 2

Comparison of 'Gala Surf' to 'Galaval' (U.S. Plant Pat. No. 19,909):

| | "Gala Surf' | 'Galaval' |
|---|---|---|
| Fruit: Overcolor | Very dark purple red | Dark red |
| Fruit: Amount of overcolor | Very high | High |

BRIEF DESCRIPTION OF THE PHOTOGRAPHS

Figure 1:
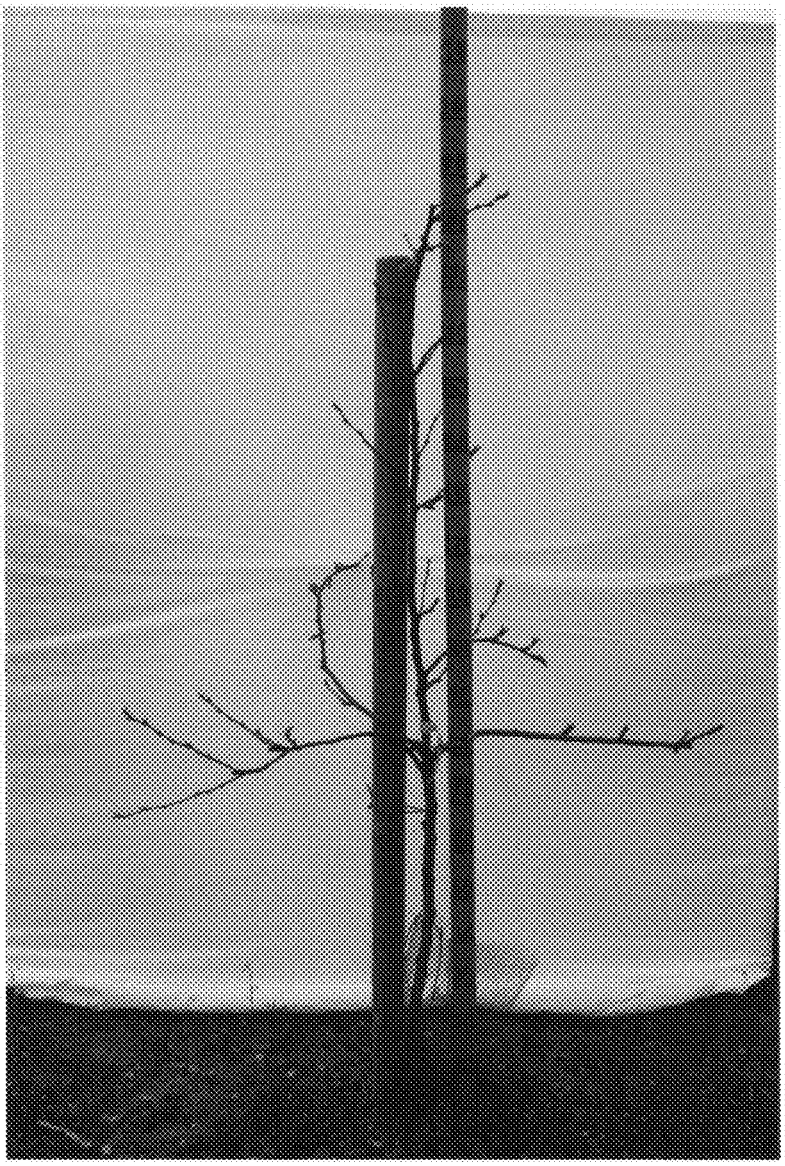
Figure 2:
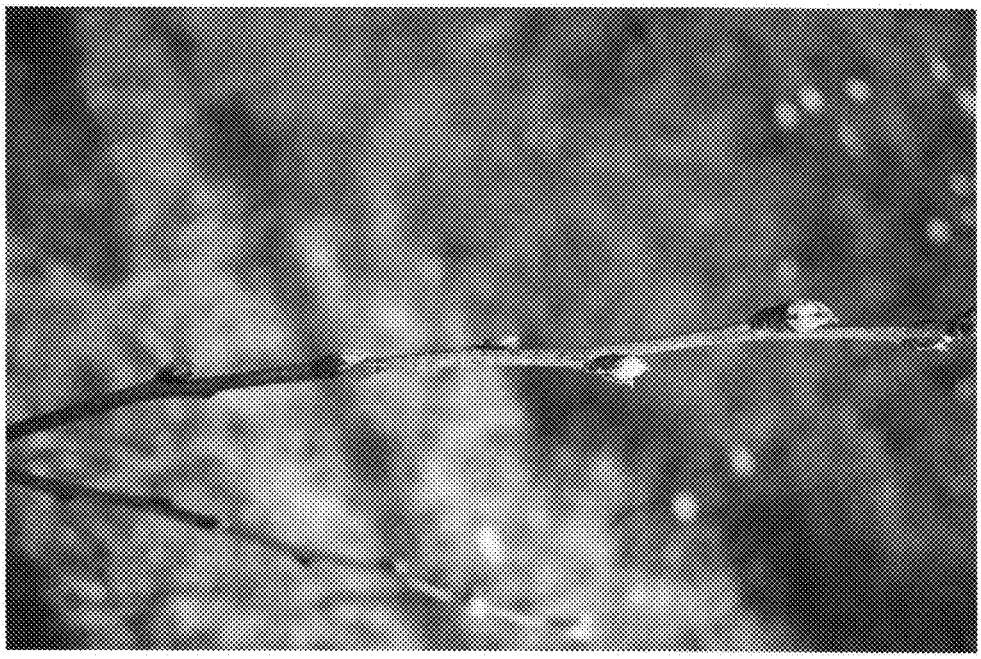
Figure 3:
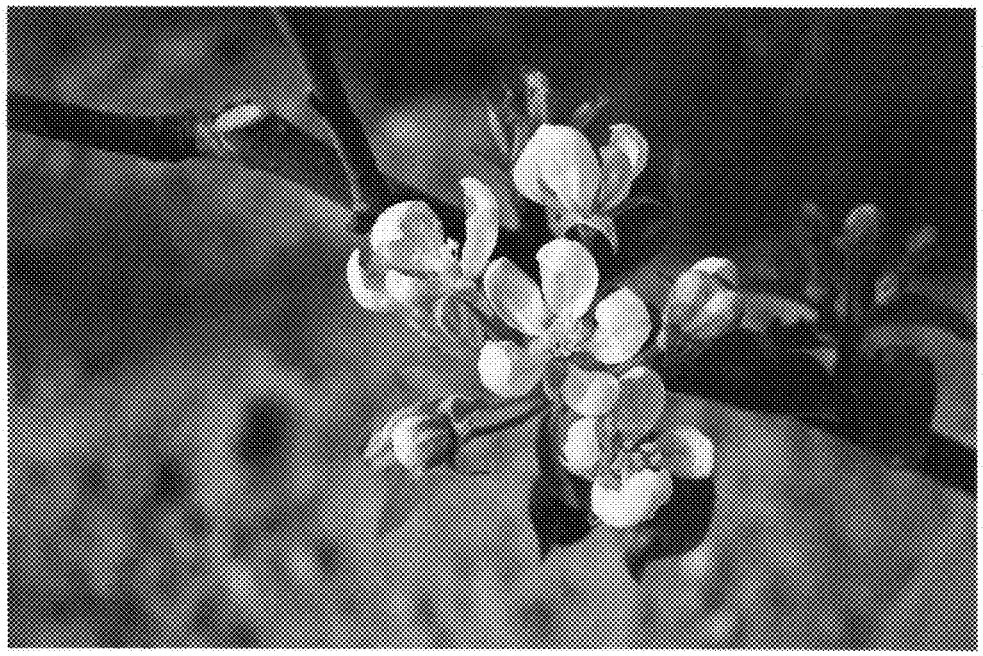
Figure 4:
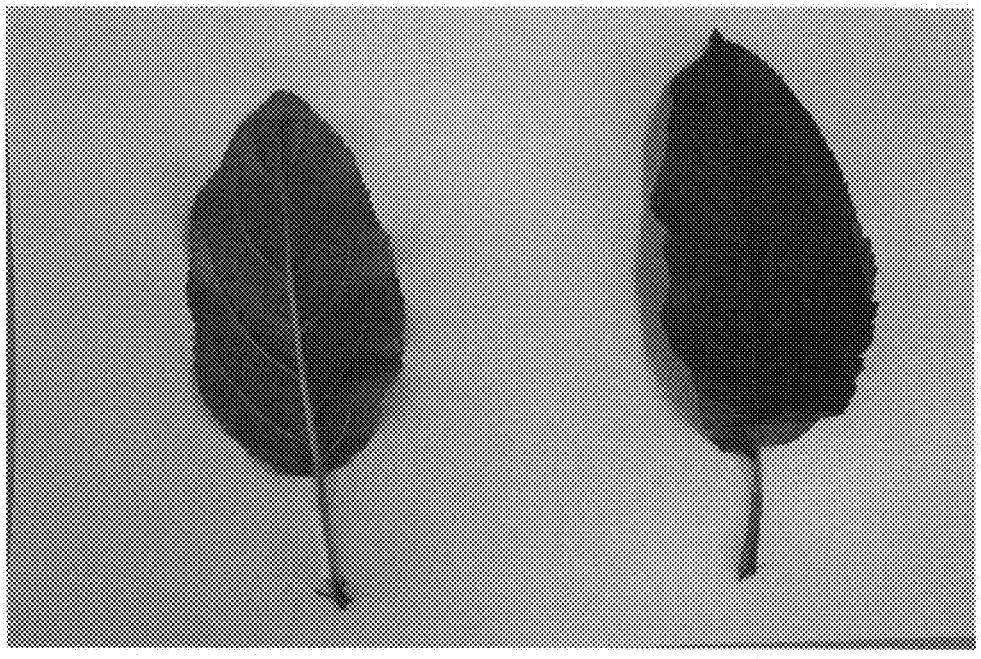
Figure 5:
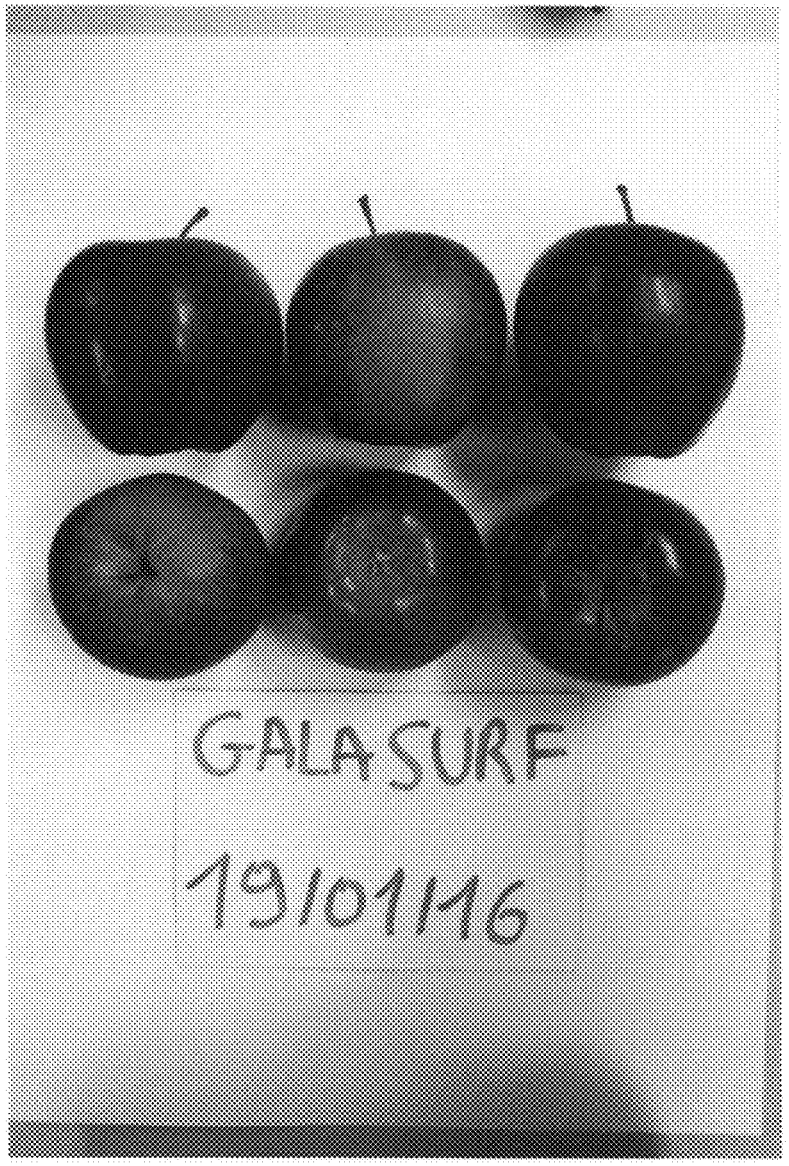

FIG. 1. shows a 'Gala Surf' tree;
FIG. 2 shows shoots and buds on a 'Gala Surf' tree;
FIG. 3 shows blossoms and leaves on a 'Gala Surf' tree;
FIG. 4 shows leaves of 'Gala Surf'; and
FIG. 5 shows fruit of 'Gala Surf'.

DETAILED BOTANICAL DESCRIPTION OF THE VARIETY

The following-detailed botanical description is based on observations made during 2015 and 2016 at Seiches sur le Loir, France of 1 and 2 year old trees grown on Pajam® 2 Cepiland rootstock (not patented). All colors are described according to The Royal Horticultural Society Mini Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor*.—Medium.
- *Type*.—Ramified.
- *Habit*.—Spreading.
- *Height*.—2.20 m.
- *Trunk diameter* (*at* 30 *cm above the graft*).—Medium, average 40 mm.
- *Bark texture*.—Smooth.
- *Bark color*.—Grey N200C.

Branch (fruiting branches located at around 1 m above the graft union):
- *Length*.—Long, average 1.2 m.
- *Diameter*.—Large, average 20 mm.
- *Crotch angle*.—70° to 90°.
- *Bark color*.—Grey N200C.
- *Lenticel length*.—1 mm.
- *Lenticel color*.—Light yellow 15D.
- *Number of lenticels per cm*$^2$.—Medium, 7 lenticels per cm$^2$.
- *Lenticel shape*.—Round.

One year old shoot:
- *Length*.—Short to medium, average 20 cm.
- *Color*.—Brown N199C.
- *Pubescence*.—Medium.
- *Thickness*.—Thin, average 3.5 mm.
- *Internode length*.—Medium, 18 mm.
- *Pubescence*.—Medium.
- *Number of lenticels per cm*$^2$.—Medium, 7 lenticels/cm$^2$.
- *Lenticel diameter*.—1 mm.
- *Lenticel height*.—0.5 mm.
- *Lenticel shape*.—Round.
- *Lenticel color*.—Light yellow brown 160B.

Flower buds:
- *Quantity per spur*.—1 to 3.
- *Shape*.—Round to conical.
- *Length*.—Small to medium, average 11 mm.
- *Diameter*.—Small to medium, average 12 mm.
- *Color*.—Red purple N57A.

Flowers:
- *Diameter of fully open flower*.—Small to medium, average 30 mm.
- *Flower depth*.—17.2 mm.
- *Relative position of petal margin*.—Overlapping.
- *Number per cluster*.—5 to 6.
- *Fragrance*.—Strong.
- *Date of first bloom*.—April 15 in Loire Valley.
- *Date of full bloom*.—April 20 in Loire Valley.
- *Pollination requirement*.—Braeburn, Granny Smith or any other variety flowering at the same time.

Petals:
- *Number per flower*.—5.
- *Shape*.—Ovoid.
- *Length*.—Medium, average 17 mm.
- *Width*.—Medium, average 13 mm.
- *Apex*.—Round.
- *Base*.—Conical-pointed.
- *Margin*.—Smooth.
- *Color of upper surface*.—White N155C.
- *Color of lower surface*.—White N155B.

Pistils:
- *Quantity*.—5.
- *Length*.—Medium, average 13 mm.
- *Color*.—Yellow green N144C.

Stigma:
- *Diameter*.—Small to medium, average 0.6 mm.
- *Color*.—Yellow green 150B.

Style:
- *Size*.—Long, average 11 mm.
- *Color*.—Yellow green 145A.

Ovary:
- *Diameter*.—Medium, average 2 mm.
- *Color*.—Green 140A.

Anthers:
- *Quantity*.—Numerous, average 13 per flower.
- *Length*.—Medium, average 2.1 mm.
- *Presence of pollen*.—Present, abundant.
- *Color of pollen*.—Yellow 3C.

Pedicel:
- *Length*.—Medium to long, average 22 mm.
- *Diameter*.—Quite thin, average 1.4 mm.
- *Color*.—Green 143B.

Sepals:
- *Quantity*.—5.
- *Color of upper surface*.—Yellow Green 145A.
- *Color of lower surface*.—Light Green RHS 138D.
- *Length*.—9.8 mm.
- *Width*.—3.8 mm.
- *Sepal shape*.—Acuminate.
- *Apex shape*.—Pointed.
- *Margin*.—Smooth, pubescent.

Leaves:
- *Shape*.—Elliptic.
- *Length*.—Medium-long, average 88 mm.
- *Width*.—Narrow, average 43 mm.
- *Length/width ratio*.—Medium to large (2.05).
- *Blade margin*.—Serrate.
- *Apex*.—Acuminate.
- *Base shape*.—Oblique.
- *Color of upper surface*.—Dark green 137A (in late summer).
- *Color of lower surface*.—Green 137C (in late summer).
- *Attitude in relation to shoot*.—Outward to downward.

Petiole:
- *Length*.—Long, average 35 mm.
- *Diameter*.—Medium, average 1.5 mm.
- *Color*.—Green 137C with anythocyanin coloration dark purple red 185B at base.

Fruit:
- *Quantity per cluster*.—2 to 4.
- *Diameter*.—71 mm.
- *Height*.—61 mm.
- *Weight*.—163 g.
- *Ratio of height to width*.—Medium (0.85).
- *General shape in profile*.—Conical.
- *Position of maximum diameter*.—Middle.
- *Ribbing*.—Moderate.
- *Crowning at calyx end*.—Moderate.
- *Length of eye*.—7 mm.

*Width of eye.*—7 mm.
*Depth of eye.*—6 mm.
*Aperture of eye.*—Closed.
*Length of sepal.*—Long.
*Bloom of skin.*—Weak.
*Greasiness of skin.*—Weak.
*Ground color of skin.*—Light yellow 15D.
*Amount of over color.*—Very high.
*Over color of skin.*—Greyed-purple 187A.
*Intensity of over color.*—Dark.
*Pattern of over color.*—Only solid flush.
*Amount of russet around stalk cavity.*—Weak.
*Amount of russet on cheeks.*—Weak.
*Area of russet around eye basin.*—Weak.
*Length of stalk.*—Medium, 20 mm.
*Thickness of stalk.*—Medium, 3 mm.
*Depth of stalk cavity.*—Medium, 17 mm.
*Width of stalk cavity.*—Narrow, 30 mm.
*Depth of eye basin.*—Medium, 7 mm.
*Width of eye basin.*—Medium, 27 mm.
*Firmness of flesh.*—Medium to firm, 6.3 kg/cm$^2$.
*Flesh texture.*—Medium to fine.
*Aroma.*—Moderately aromatic and slightly sweet.
*Juiciness.*—Medium to high.
*Brix.*—11° Brix.
*Flesh color.*—Light yellow 4D.
*Stem color.*—Dark purple red 53A.

Fruit locules:
*Quantity per fruit.*—5.
*Length.*—12 mm.
*Width.*—7 mm.

Seeds:
*Quantity per fruit.*—Average 5.
*Length.*—8 mm.
*Width.*—5 mm.
*Shape.*—Truncate ovoid.
*Color.*—Dark brown 165A.

Harvest:
*Time for harvest.*—Early, last week of August in the Loire Valley.
*Number of picks.*—One to two.
*Fruit load per tree.*—60 fruits (about 10 kg) on third leaf trees in 2016.

Disease resistance/susceptibility: None noted.

Winter hardiness: Hardy in region tested, USDA Hardiness Zone 9a.

Market use: Fresh.

I claim:

1. A new and distinct apple tree as described and illustrated herein.

* * * * *